(12) United States Patent
Stites et al.

(10) Patent No.: US 11,618,767 B2
(45) Date of Patent: Apr. 4, 2023

(54) CARBOXY SUBSTITUTED GLUCOCORTICOID RECEPTOR AGONISTS

(71) Applicant: Eli Lilly and Company, Indianapolis, IN (US)

(72) Inventors: Ryan Edward Stites, Indianapolis, IN (US); Jacqueline Mary Wurst, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 17/700,824

(22) Filed: Mar. 22, 2022

(65) Prior Publication Data

US 2022/0306681 A1    Sep. 29, 2022

Related U.S. Application Data

(60) Provisional application No. 63/164,592, filed on Mar. 23, 2021.

(51) Int. Cl.
*C07J 71/00* (2006.01)

(52) U.S. Cl.
CPC .................... *C07J 71/0031* (2013.01)

(58) Field of Classification Search
CPC .................................... C07J 71/0031
See application file for complete search history.

(56) References Cited

U.S. PATENT DOCUMENTS 8,524,697 B2    9/2013    Anthes et al.

FOREIGN PATENT DOCUMENTS

| WO | 2006/138212 A1 | 12/2006 |
| WO | 2009/069032 A2 | 6/2009 |
| WO | 2009/085879 A2 | 7/2009 |
| WO | 2009/108118 A1 | 9/2009 |
| WO | 2017/132103 A2 | 8/2017 |
| WO | 2017/210471 A1 | 12/2017 |
| WO | 2018/089373 A2 | 5/2018 |
| WO | 2019/106608 A1 | 6/2019 |
| WO | 2019/106609 A1 | 6/2019 |
| WO | 2021/216913 A1 | 10/2021 |

OTHER PUBLICATIONS

Millan, D. S. et al., "Design and Synthesis of Long Acting Inhaled Corticosteroids for the Treatment of Asthma," Bioorganic & Medicinal Chemistry Letters, vol. 21, pp. 5826-5830 (2011).

*Primary Examiner* — Barbara P Badio
(74) *Attorney, Agent, or Firm* — Gabriel Magallanes

(57) ABSTRACT

The present invention provides a compound of Formula I:

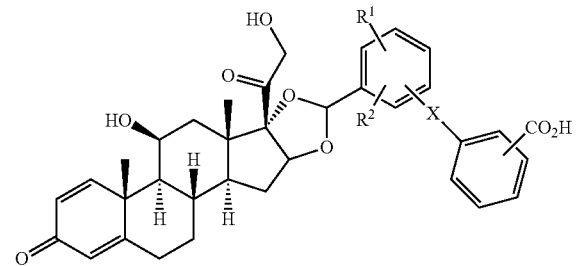

Formula I wherein $R^1$ is H, halogen, C1-C3 alkyl, or C1-C3 alkoxy;
$R^2$ is H or halogen; and
X is O, $OCH_2$, or $CH_2$, or a pharmaceutically acceptable salt thereof, wherein the compound of Formula I, or pharmaceutically acceptable salt thereof is useful for treating autoimmune and inflammatory diseases, such as atopic dermatitis, rheumatoid arthritis, and lupus nephritis.

24 Claims, No Drawings

CARBOXY SUBSTITUTED GLUCOCORTICOID RECEPTOR AGONISTS

The present disclosure provides compounds that are glucocorticoid receptor agonists and are useful for the treatment of autoimmune and inflammatory diseases, such as atopic dermatitis, inflammatory bowel disease, systemic lupus erythematosus, lupus nephritis, and rheumatoid arthritis, processes for preparing these compounds, pharmaceutical compositions comprising these compounds, and methods of using these compounds and compositions are also provided.

Atopic dermatitis is a chronic, pruritic relapsing and remitting inflammatory skin disease that occurs frequently in children, but also affects many adults. Current treatments of atopic dermatitis include light therapy, topical creams containing corticosteroids or calcineurin inhibitors, or a subcutaneous injectable biologic known as dupilumab. In spite of progress made in treating atopic dermatitis, there remains a significant need for new compounds to treat atopic dermatitis and other inflammatory and autoimmune diseases.

WO2017/210471 discloses certain glucocorticoid receptor agonists and immunoconjugates thereof useful for treating autoimmune or inflammatory diseases. WO2018/089373 discloses novel steroids, protein conjugates thereof, and methods for treating diseases, disorders, and conditions comprising administering the steroids and conjugates.

The present invention provides certain novel compounds which are glucocorticoid receptor agonists. In addition, the present invention provides certain novel compounds which are glucocorticoid receptor agonists useful in the treatment of autoimmune and inflammatory diseases such as atopic dermatitis, inflammatory bowel disease, rheumatoid arthritis, systemic lupus erythematosus, and lupus nephritis.

Accordingly, in one embodiment, the invention provides a compound of Formula I:

Formula I

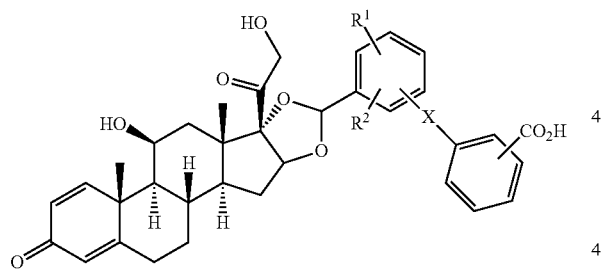

wherein $R^1$ is H, halogen, C1-C3 alkyl, or C1-C3 alkoxy;
$R^2$ is H or halogen; and
X is O, $OCH_2$, or $CH_2$,
or a pharmaceutically acceptable salt thereof.

In one embodiment, the invention provides a compound of Formula Ia:

Formula Ia

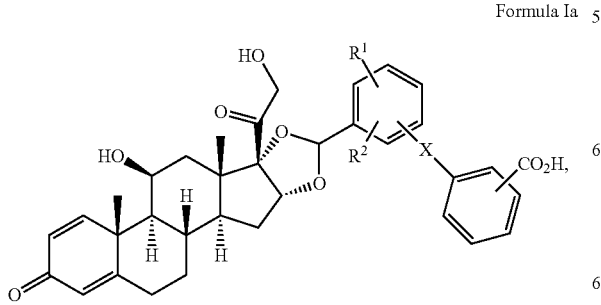

or a pharmaceutically acceptable salt thereof.

In one embodiment, the invention provides a compound of Formula Ib:

Formula Ib

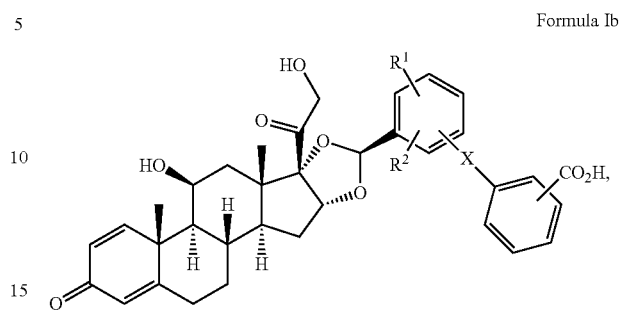

or a pharmaceutically acceptable salt thereof.

In one embodiment, the invention provides a compound of Formula Ic:

Formula Ic

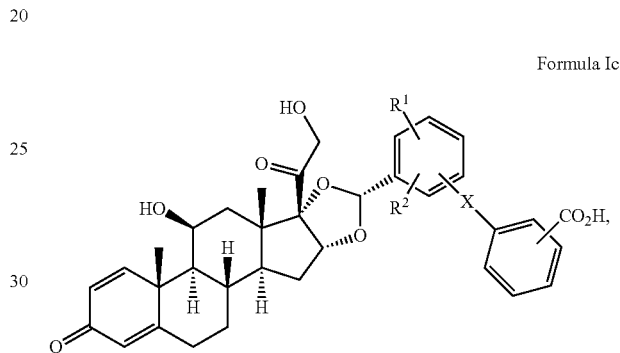

or a pharmaceutically acceptable salt thereof.

In a further embodiment, the invention provides a compound of Formula Ib(i):

Formula Ib(i)

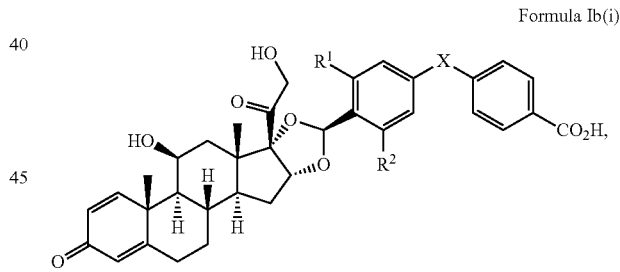

or a pharmaceutically acceptable salt thereof.

In a further embodiment, the invention provides a compound of Formula Ic(i):

Formula Ic(i)

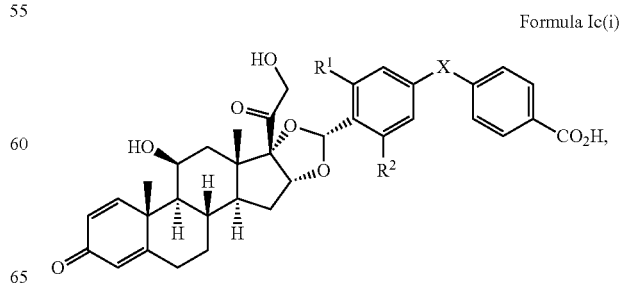

or a pharmaceutically acceptable salt thereof.

In a further embodiment, the invention provides a compound of Formula Ib(ii):

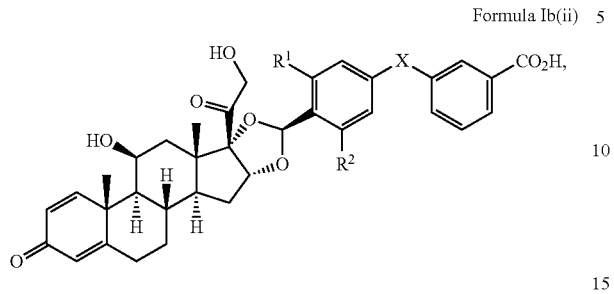

Formula Ib(ii)

or a pharmaceutically acceptable salt thereof.

In a further embodiment, the invention provides a compound of Formula Ic(ii):

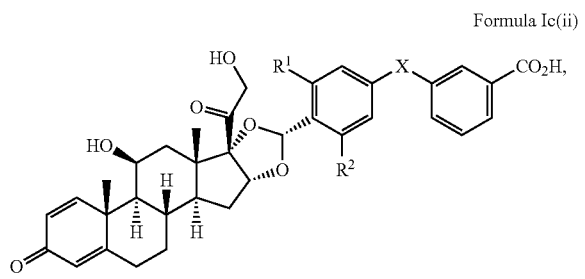

Formula Ic(ii)

or a pharmaceutically acceptable salt thereof.

In a further embodiment, the invention provides a compound of Formula Ib(iii):

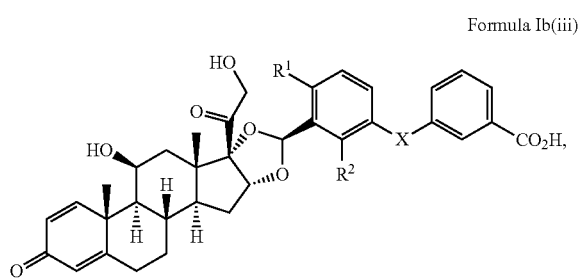

Formula Ib(iii)

or a pharmaceutically acceptable salt thereof.

In a further embodiment, the invention provides a compound of Formula Ic(iii):

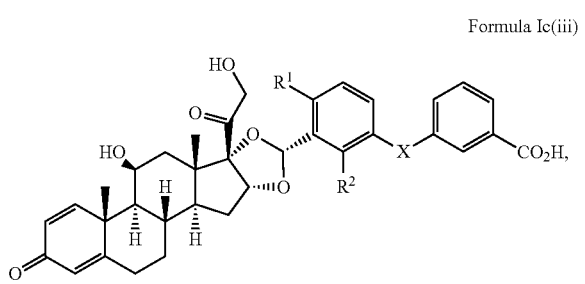

Formula Ic(iii)

or a pharmaceutically acceptable salt thereof.

In a further embodiment, the invention provides a compound of Formula Ib(iv):

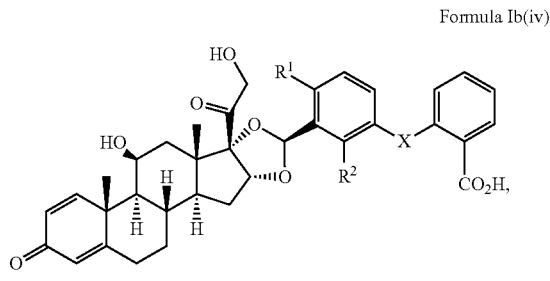

Formula Ib(iv)

or a pharmaceutically acceptable salt thereof.

In a further embodiment, the invention provides a compound of Formula Ic(iv):

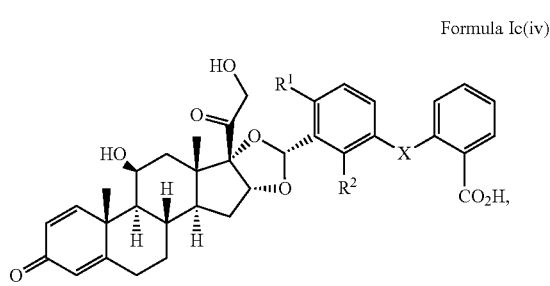

Formula Ic(iv)

or a pharmaceutically acceptable salt thereof.

In an embodiment X is O.
In an embodiment X is $OCH_2$.
In an embodiment X is $CH_2$.
In an embodiment $R^1$ is F.
In an embodiment $R^1$ is H.
In an embodiment $R^1$ is $CH_3$.
In an embodiment $R^1$ is $OCH_3$.
In an embodiment $R^2$ is H.
In an embodiment $R^2$ is F.
In an embodiment $R^2$ is absent.
In an embodiment X is $CH_2$, $R^1$ is F, and $R^2$ is H.
In an embodiment X is O, and $R^1$ and $R^2$ are each H.
In an embodiment X is $OCH_2$, $R^1$ is $CH_3$, and $R^2$ is F.
In an embodiment X is $OCH_2$, $R^1$ is $OCH_3$, and $R^2$ is F.
In one embodiment, the invention provides a compound of Formula II:

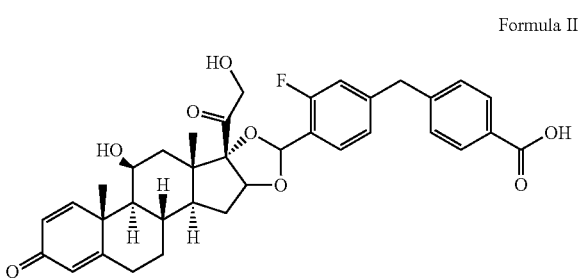

Formula II or a pharmaceutically acceptable salt thereof.

In a particular embodiment, the invention provides a compound of Formula IIa:

Formula IIa

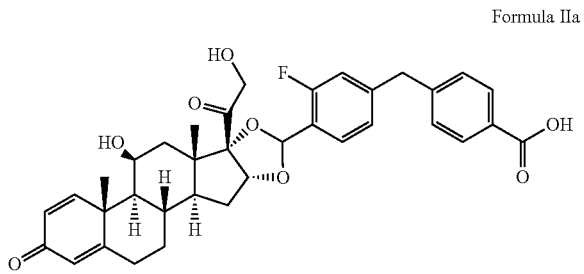

or a pharmaceutically acceptable salt thereof.

In a particular embodiment, the invention provides a compound of Formula IIb:

Formula IIb

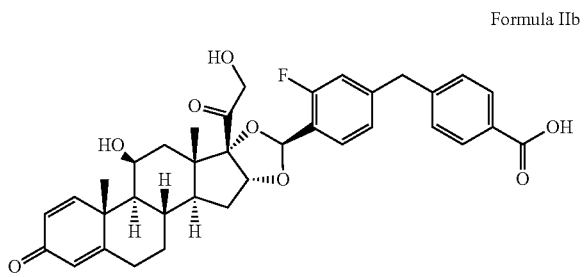

or a pharmaceutically acceptable salt thereof.

In a particular embodiment, the invention provides a compound of Formula IIc:

Formula IIc

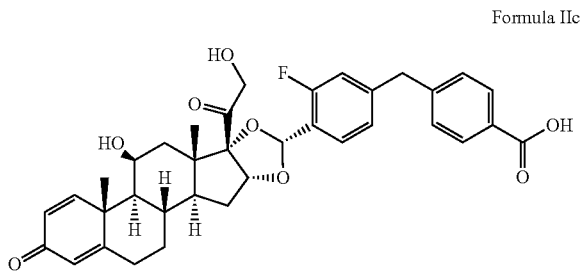

or a pharmaceutically acceptable salt thereof.

In an embodiment, the present invention also provides a method of treating an inflammatory disease in a patient in need of such treatment, comprising administering to the patient an effective amount of a compound of Formula I, or a pharmaceutically acceptable salt thereof. In an embodiment, the present invention also provides a method of treating an autoimmune disease in a patient in need of such treatment, comprising administering to the patient an effective amount of a compound of Formula I, or a pharmaceutically acceptable salt thereof. In an embodiment, the present invention also provides a method of treating atopic dermatitis in a patient in need of such treatment, comprising administering to the patient an effective amount of a compound of Formula I, or a pharmaceutically acceptable salt thereof. In an embodiment, the present invention further provides a method of treating inflammatory bowel disease in a patient in need of such treatment, comprising administering to the patient an effective amount of a compound of Formula I, or a pharmaceutically acceptable salt thereof. In an embodiment, the present invention further provides a method of treating rheumatoid arthritis in a patient in need of such treatment, comprising administering to the patient an effective amount of a compound of Formula I, or a pharmaceutically acceptable salt thereof. In an embodiment, the present invention also provides a method of treating systemic lupus erythematosus in a patient in need of such treatment, comprising administering to the patient an effective amount of a compound of Formula I, or a pharmaceutically acceptable salt thereof. In an embodiment, the present invention also provides a method of treating lupus nephritis in a patient in need of such treatment, comprising administering to the patient an effective amount of a compound of Formula I, or a pharmaceutically acceptable salt thereof.

In an embodiment, the present invention further provides a compound of Formula I, or a pharmaceutically acceptable salt thereof for use in therapy. In an embodiment, the present invention provides a compound of Formula I, or a pharmaceutically acceptable salt thereof for use in treating an inflammatory disease. In an embodiment, the present invention provides a compound of Formula I, or a pharmaceutically acceptable salt thereof for use in treating an autoimmune disease. In an embodiment, the present invention provides a compound of Formula I, or a pharmaceutically acceptable salt thereof, for use in treating atopic dermatitis. In an embodiment, the present invention provides a compound of Formula I, or a pharmaceutically acceptable salt thereof, for use in treating rheumatoid arthritis. In an embodiment, the present invention provides a compound of Formula I, or a pharmaceutically acceptable salt thereof, for use in treating inflammatory bowel disease. In an embodiment, the present invention provides a compound of Formula I, or a pharmaceutically acceptable salt thereof, for use in treating lupus nephritis. In an embodiment, the present invention provides a compound of Formula I, or a pharmaceutically acceptable salt thereof, for use in treating systemic lupus erythematosus.

In an embodiment, the present invention also provides the use of a compound of Formula I, or a pharmaceutically acceptable salt thereof, for the manufacture of a medicament for treating an inflammatory disease. In an embodiment, the present invention also provides the use of a compound of Formula I, or a pharmaceutically acceptable salt thereof, for the manufacture of a medicament for treating an autoimmune disease. In an embodiment, the present invention provides the use of a compound of Formula I, or a pharmaceutically acceptable salt thereof, for the manufacture of a medicament for treating atopic dermatitis. In an embodiment, the present invention provides the use of a compound of Formula I, or a pharmaceutically acceptable salt thereof, for the manufacture of a medicament for treating rheumatoid arthritis. In an embodiment, the present invention further provides the use of a compound of Formula I, or a pharmaceutically acceptable salt thereof, for the manufacture of a medicament for treating inflammatory bowel disease. In an embodiment, the present invention further provides the use of a compound of Formula I, or a pharmaceutically acceptable salt thereof, for the manufacture of a medicament for treating lupus nephritis. In an embodiment, the present invention also provides the use of a compound of Formula I, or a pharmaceutically acceptable salt thereof, for the manufacture of a medicament for treating systemic lupus erythematosus.

In an embodiment, the present invention further provides a pharmaceutical composition, comprising a compound of Formula I, or a pharmaceutically acceptable salt thereof, with one or more pharmaceutically acceptable carriers, diluents, or excipients. In an embodiment, the present invention further provides a process for preparing a pharmaceutical composition, comprising admixing a compound of Formula I, or a pharmaceutically acceptable salt thereof, with one or more pharmaceutically acceptable carriers, diluents, or excipients. In an embodiment, the present invention also encompasses novel intermediates and processes for the synthesis of compounds of Formula I.

As used herein, the terms "treating", "treatment", or "to treat" includes restraining, slowing, stopping, or reversing the progression or severity of an existing symptom or disorder.

As used herein, the term "patient" refers to a mammal, in particular a human.

As used herein, the term "effective amount" refers to the amount or dose of compound of the invention, or a pharmaceutically acceptable salt thereof which, upon single or multiple dose administration to the patient, provides the desired effect in the patient under diagnosis or treatment.

An effective amount can be determined by one skilled in the art by the use of known techniques and by observing results obtained under analogous circumstances. In determining the effective amount for a patient, a number of factors are considered by the attending diagnostician, including, but not limited to: the species of patient; its size, age, and general health; the specific disease or disorder involved; the degree of or involvement or the severity of the disease or disorder; the response of the individual patient; the particular compound administered; the mode of administration; the bioavailability characteristics of the preparation administered; the dose regimen selected; the use of concomitant medication; and other relevant circumstances.

As used herein, it is understood that Formula I encompasses Formulas Ia, Ib, Ic, Ib(i), Ib(ii), Ib(iii), Ib(iv), Ic(i), Ic(ii), Ic(iii), Ic(iv), II, IIa, IIb, and IIc, and all references to Formula I herein should be read as including Formulas Ia, Ib, Ic, Ib(i), Ib(ii), Ib(iii), Ib(iv), Ic(i), Ic(ii), Ic(iii), Ic(iv), II, IIa, IIb, and IIc.

As used herein "halogen" refers to F, Cl, Br, and I.

As used herein "C1-C3 alkyl" refers to $CH_3$, $CH_2CH_3$, $CH_2CH_2CH_3$, and $CH(CH_3)_2$.

As used herein "C1-C3 alkoxy" refers to $OCH_3$, $OCH_2CH_3$, $OCH_2CH_2CH_3$, and $OCH(CH_3)_2$.

In addition, a compound of the present invention can be conjugated with an antibody to form an antibody drug conjugate (ADC) by methods understood by one of skill in the art. One example of such conjugation would include connection of a compound of the present invention to an antibody via a linker compound. Linker compounds known to those of skill in the art include, for example, cleavable linkers and noncleavable linker. Such an ADC can deliver the compound of the present invention to specific target tissues or cells. Accordingly, provided herein are also ADCs comprising a compound of Formula I. In some embodiments, the compound of Formula I is conjugated to an antibody via a linker, e.g., a cleavable linker or a noncleavable linker. Such ADCs can be administered by injection, e.g., intravenous or subcutaneous injection.

The compounds or conjugates of the present invention can be formulated as pharmaceutical compositions administered by any route which makes the compound or conjugate bioavailable including topical administration or subcutaneous administration. Such pharmaceutical compositions, including ADCs, can be prepared using techniques and methods known in the art (See, e.g., Remington: The Science and Practice of Pharmacy, A. Adej are, Editor, $23^{nd}$ Edition, published 2020, Elsevier Science; WO 2017/062271, and WO 2017/210471).

Included within the scope of the present invention is a pharmaceutically acceptable salt of Formula I. A pharmaceutically acceptable salt of a compound of the invention, such as a compound of Formula I can be formed, for example, by reaction of an appropriate free acid of a compound of the invention with an appropriate pharmaceutically acceptable base in a suitable solvent such as diethyl ether under standard conditions well known in the art. See, for example, Berge, S. M., et al., "Pharmaceutical Salts," *Journal of Pharmaceutical Sciences,* 66: 1-19, (1977).

Certain abbreviations are defined as follows: "aq" refers to aqueous; "DMSO" refers to dimethyl sulfoxide; "EtOAc" refers to ethyl acetate; "THF" refers to tetrahydrofuran; "DMF" refers to N,N-dimethylformamide; "DCM" refers to methylene chloride or dichloromethane; "IPA" refers to isopropyl alcohol; "MeOH" refers to methanol or methyl alcohol; "ACN" refers to acetonitrile; "C18" refers to octadecylsilane; "DMEA" refers to dimethylethylamine; "MTBE" refers to methyl tert-butyl ether; "LDA" refers to lithium diisopropylamide; "Pd(dppf)Cl$_2$" refers to [1,1'-bis(diphenylphosphino)ferrocene]dichloropalladium(II); "g" refers to gram or grams; "rt" refers to room temperature; "h" refers to hour or hours; "min" refers to minute or minutes; "mL" refers to milliliter or milliliters; "mol" refers to mole or moles; "mmol" refers to millimole or millimoles; "nm" refers to nanometer; "SFC" refers to supercritical fluid chromatography; "ES/MS" refers to Electrospray Mass Spectrometry; "m/z" refers to mass-to-charge ratio for mass spectroscopy; "NMR" refers to nuclear magnetic resonance; and "ROE" refers to rotating-frame Overhauser enhancement.

The compounds of the present invention, or salts thereof, may be readily prepared by a variety of procedures known to one of ordinary skill in the art, some of which are illustrated in the preparations and examples below. One of ordinary skill in the art recognizes that the specific synthetic steps for each of the routes described may be combined in different ways, or in conjunction with steps from different schemes, to prepare compounds of the invention, or salts thereof. The product of each step can be recovered by conventional methods well known in the art, including extraction, evaporation, precipitation, chromatography, filtration, trituration, and crystallization. All substituents unless otherwise indicated, are as previously defined. The reagents and starting materials are readily available to one of ordinary skill in the art. The following preparations, examples, and assays further illustrate the invention, but should not be construed to limit the scope of the invention in any way.

Scheme 1

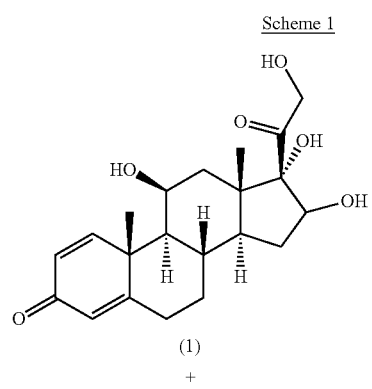

(1)

+

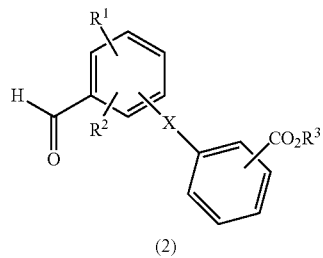

(2)

→

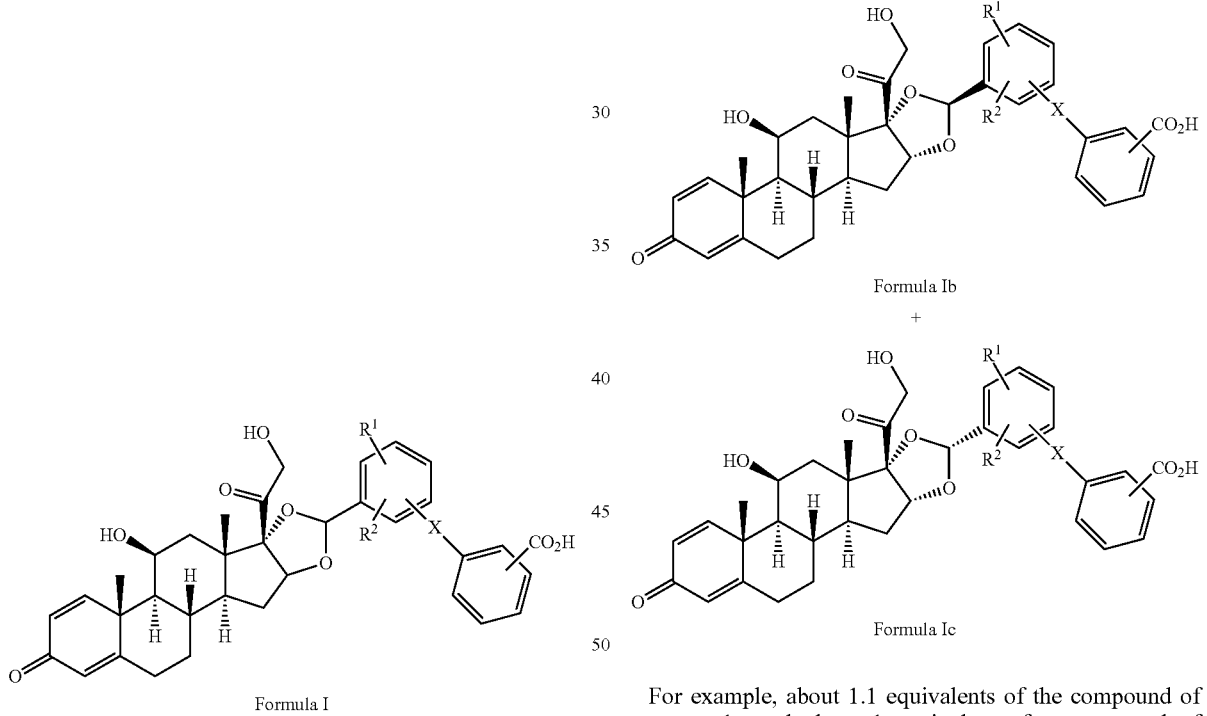

Formula I

Scheme 1A

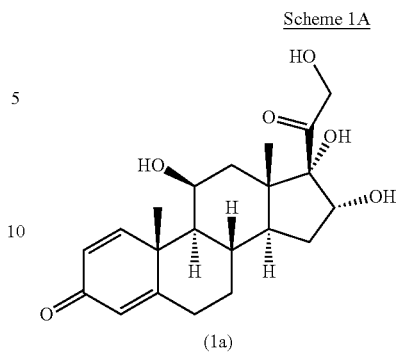

(1a)

+

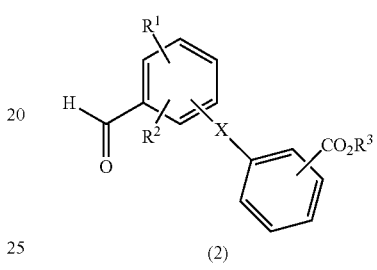

(2)

→

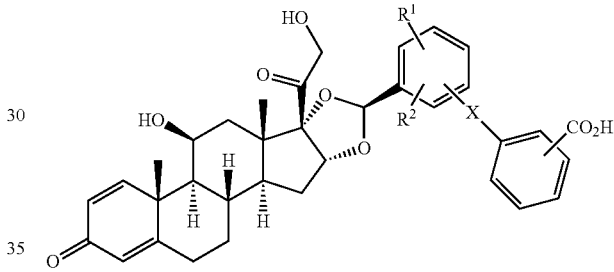

Formula Ib

+

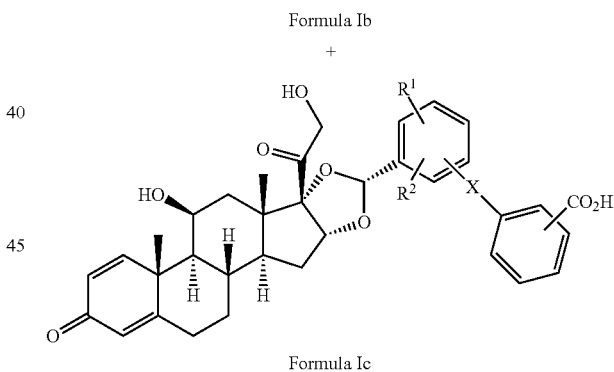

Formula Ic

In Scheme 1, the compound of structure 1 is reacted with an aldehyde of structure 2 wherein $R^3$ is hydrogen or a suitable alkyl group, such as a tert-butyl or methyl, under conditions well known to one of ordinary skill in the art to provide the compound of Formula I.

More specifically, as shown in Scheme 1A below, the compound of structure 1a is reacted with an aldehyde of structure 2 wherein $R^3$ is hydrogen or a suitable alkyl group, such as a tert-butyl or methyl, under conditions well known to one of ordinary skill in the art to provide the compounds of Formula Ib and Formula Ic.

For example, about 1.1 equivalents of the compound of structure 1a and about 1 equivalent of a compound of structure 2 wherein $R^3$ is hydrogen or a suitable alkyl group, such as a tert-butyl group, are suspended in a suitable organic solvent, such as acetonitrile. The suspension is cooled to about −10° C. and then treated with about 5 equivalents of a suitable acid, such as perchloric acid (70% in water). The reaction mixture is then warmed to room temperature and allowed to stir for about 1 hour. Additional organic solvents may be added, such as acetonitrile and dimethylformamide, and the mixture is allowed to stir for about 2 additional hours. The reaction is then quenched using standard conditions, such as with saturated aqueous sodium bicarbonate and the products are isolated using standard techniques well known in the art, such as extraction with a suitable organic solvent, such as methylene chloride:

isopranol (9:1), drying the organic extracts over magnesium sulfate, filtering, and concentration under vacuum to provide the crude product mixture. This crude mixture can be purified and the products of Formula Ib and Formula Ic separated using techniques well know in the art, such as chromatography, for example reverse phase chromatography with a suitable eluent, such as 2:1 10 mM ammonium bicarbonate water+5% methanol:acetonitrile.

over sodium sulfate, filtered, and concentrated to a crude residue. The residue was purified by normal phase purification (silica gel), eluting with 9:1 hexanes:ethyl acetate to give the title compound (18.7 g, 86% yield). ES/MS m/z 257.0 (M-tBu-H).

The following compound in Table 1 was prepared in a manner essentially analogous to the procedure described in Preparation 1.

TABLE 1

| Prep. No. | Name | Structure | ES/MS (m/z) (M + H) |
|---|---|---|---|
| 2 | tert-butyl 3-(3-fluoro-4-formylbenzyl)benzoate | 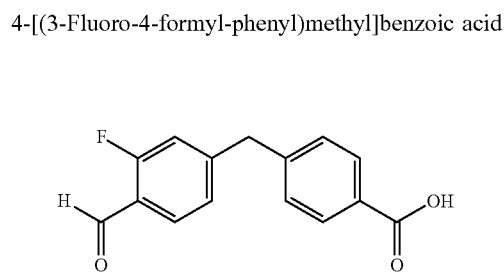 | 259.0 (M − tBu + H) |

Scheme 2

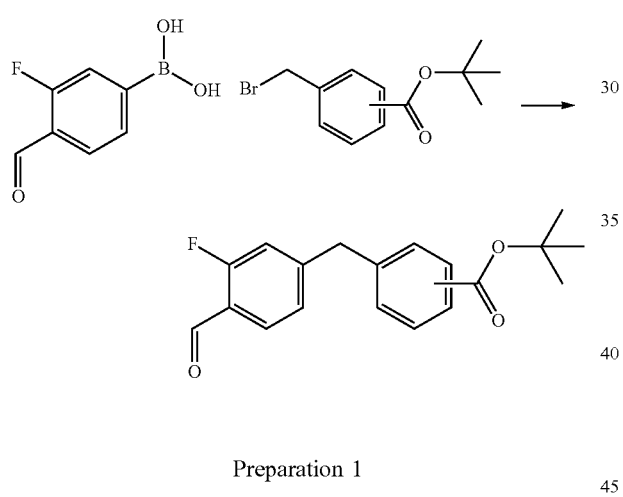

Preparation 1 tert-Butyl 4-[(3-fluoro-4-formyl-phenyl)methyl]benzoate

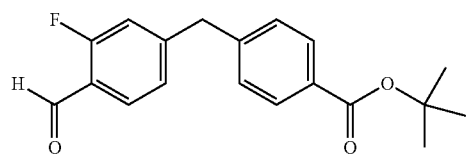 [SMILES: CC(C)(C)OC(=O)c1ccc(Cc2ccc(C=O)c(F)c2)cc1]

To a 20 mL sealed tube was added (3-fluoro-4-formyl-phenyl)boronic acid (10 g, 60 mmol), tert-butyl 4-(bromomethyl)benzoate (18 g, 66 mmol), potassium carbonate (27 g, 200 mmol), tetrakis(triphenylphosphene)palladium(0) (2.1 g, 1.8 mmol), and THF (100 mL):water (40 mL). The reaction was heated to 95° C. After 1 h, the reaction was diluted with water and EtOAc. The layers were separated and the aqueous layer was extracted with EtOAc (2×). The combined organic extracts were washed with brine, dried Preparation 3

4-[(3-Fluoro-4-formyl-phenyl)methyl]benzoic acid tert-Butyl 4-[(3-fluoro-4-formyl-phenyl)methyl]benzoate (16 g, 51 mmol, preparation 1) was dissolved in DCM (300 mL) and cooled to 0° C. Trifluoroacetic acid (150 mL) was added dropwise and the reaction was warmed to room temperature. After 1 h, the reaction was concentrated in vacuo and the off-white solid was triturated with diethyl ether/hexanes. The resulting solid was collected by filtration and dried in a vacuum oven to provide the title compound (13.1 g, 96% yield). ES/MS m/z 257.0 (M−H).

Scheme 3

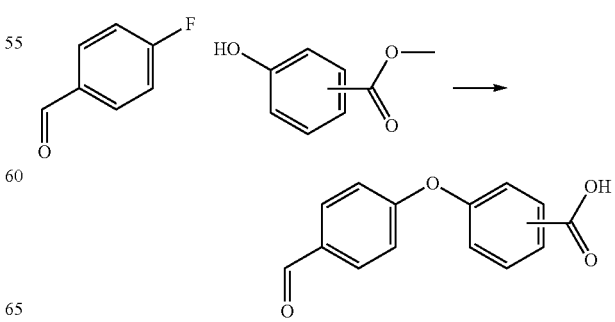

Preparation 4

4-(4-Formylphenoxy)benzoic Acid

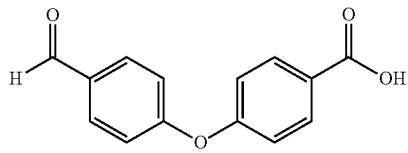 [SMILES: O=Cc1ccc(Oc2ccc(C(=O)O)cc2)cc1]

To a microwave vial were added 4-fluorobenzaldehyde (0.63 g, 5.0 mmol), methyl 4-hydroxybenzoate (0.81 g, 5.3 mmol), DMF (15 mL), and potassium carbonate (0.83 g, 6.0 mmol). The reaction was microwaved at 150° C. for 1 h and cooled to rt. The solution was partitioned between EtOAc and water. The organic layer was isolated, washed with saturated aq. sodium chloride (2×), saturated aq NaHCO$_3$, dried over MgSO$_4$, filtered, and was concentrated to a colorless oil. To the crude oil, hexanes (50 mL) were added to yield a white semi-solid. It was then sonicated, chilled to 0° C., and suction filtered to isolate a white solid. The white solid was washed with hexanes and dried under vacuum.

The white solid was dissolved in methanol (8 mL), and sodium hydroxide in water (5M, 2 mL) was added. The solution was heated to 50° C. for 2 h. The reaction was cooled to rt, diluted with water (10 mL), and acidified to pH 4 with 5N aq HCl. A white solid was collected via suction filtration, washed with water, and further dried under vacuum to give the title compound (790 mg, 84% yield). MS m/z 241.0 (M−H).

The following compound in Table 2 was prepared in a manner essentially analogous to the procedure described in Preparation 4.

TABLE 2

| Prep. No. | Name | Structure | ES/MS (m/z) (M − H) |
|---|---|---|---|
| 5 | 3-(4-formylphenoxy)benzoic acid | 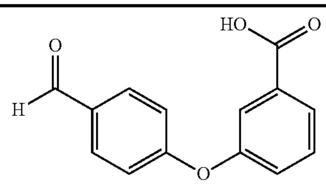 | 241.0 |

Preparation 6

6-Bromo-2-fluoro-3-methoxy-benzaldehyde

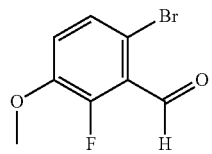

Two reactions were carried out in parallel. To a solution of 4-bromo-2-fluoro-1-methoxybenzene (250 g, 1.2 mol) in THF (1500 mL) was added LDA (2 M, 730 mL) slowly at −78° C. over 30 min. After an additional 30 min, DMF (140 mL, 1.8 mol) was added at −78° C. slowly over 30 min. After 1 h, the two reactions were combined and the mixture was diluted with aq citric acid (2000 mL) and extracted with EtOAc (1500 mL×2). The combined organic layers were washed with saturated aq sodium chloride (1000 mL) and concentrated under reduced pressure to give a residue. The residue was triturated with petroleum ether (1000 mL) at rt over 12 h to give the title compound (382 g, 67% yield). ES/MS m/z 233.9 (M+H).

Preparation 7

2-Fluoro-3-methoxy-6-methyl-benzaldehyde

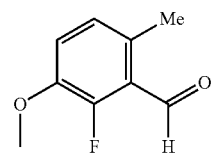

Three reactions were carried out in parallel. 6-Bromo-2-fluoro-3-methoxy-benzaldehyde (120 g, 5.3 mol, see Preparation 6), methylboronic acid (47 g, 7.9 mol), Pd(dppf)Cl$_2$ (12 g, 0.02 mol), and Cs$_2$CO$_3$ (340 g, 1.1 mol) were added in dioxane (600 mL) and water (120 mL). The mixture was stirred at 120° C. After 12 h, the three reactions were combined and the mixture was diluted with saturated aq NH$_4$Cl solution (1000 mL) and extracted with MTBE (1500 mL×2). The combined organic layers were washed with saturated aq sodium chloride (1000 mL) and concentrated under reduced pressure to give a residue. The residue was purified by normal phase chromatography, eluting with 40:1 petroleum ether:EtOAc to give the title compound (180 g, 59% yield). ES/MS m/z 169.3 (M+H).

Preparation 8

2-Fluoro-3-hydroxy-6-methyl-benzaldehyde

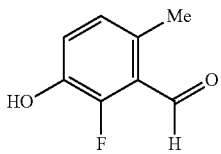 [SMILES: Cc1ccc(O)c(F)c1C=O]

2-Fluoro-3-methoxy-6-methyl-benzaldehyde (175 g, 1.0 mol, see Preparation 7) was added into DCM (1050 mL), and BBr$_3$ (200 mL, 2.1 mol) was added slowly into the solution at 0° C. The reaction was stirred at rt. After 1 h, the mixture was diluted with saturated aq sodium bicarbonate (1000 mL) until pH=7-8 and was then extracted with MTBE (1500 mL×2). The combined organic layers were washed with saturated aq sodium chloride (1000 mL) and concentrated under reduced pressure to give the title compound (110 g, 68% yield). ES/MS m/z 154.9 (M+H).

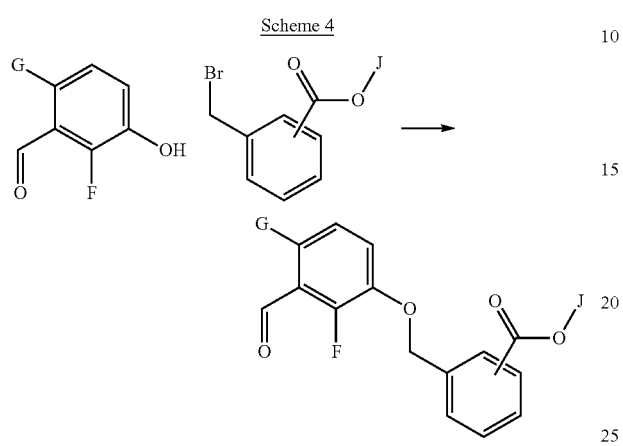

Scheme 4

Wherein G is methyl or methoxy.
Wherein J is methyl or tert-butyl.

Preparation 9 tert-Butyl 3-((2-fluoro-3-formyl-4-methylphenoxy)methyl)benzoate

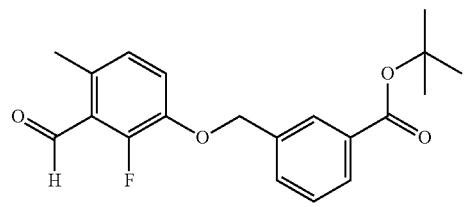 [SMILES: Cc1ccc(OCc2cccc(C(=O)OC(C)(C)C)c2)c(F)c1C=O]

A mixture of 2-fluoro-3-hydroxy-6-methyl-benzaldehyde (300 mg, 1.9 mmol, see preparation 8), tert-butyl 3-(bromomethyl)benzoate (500 mg, 1.8 mmol), and cesium carbonate (1.2 g, 3.7 mmol) in DMF (6 mL) was stirred at rt overnight. The mixture was diluted with EtOAc and water. The organic solution was washed with three portions water, one portion saturated aq sodium chloride, dried over $Na_2SO_4$, filtered, and evaporated to give the crude residue. The residue was purified by normal phase purification, eluting with 9:1 hexanes:ethyl acetate to give the title compound (250 mg, 40% yield). MS m/z 362.0 (M+$NH_4^+$).

The following compounds in Table 3 were prepared in a manner essentially analogous to the procedure described in Preparation 9.

TABLE 3

| Prep. No. | Name | Structure | ES/MS (m/z) (M + H) |
|---|---|---|---|
| 10 | tert-butyl 3-((2-fluoro-3-formyl-4-methoxyphenoxy)methyl)benzoate | 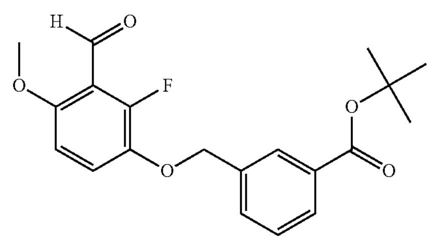 [SMILES: COc1ccc(OCc2cccc(C(=O)OC(C)(C)C)c2)c(F)c1C=O] | 378.0 (M + $NH_4^+$) |
| 11 | methyl 2-((2-fluoro-3-formyl-4-methoxyphenoxy)methyl)benzoate | 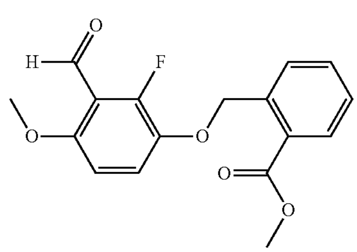 [SMILES: COC(=O)c1ccccc1COc1ccc(OC)c(C=O)c1F] | 319.0 |
| 12 | methyl 2-((2-fluoro-3-formyl-4-methylphenoxy)methyl)benzoate | 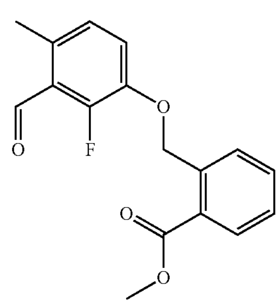 [SMILES: COC(=O)c1ccccc1COc1ccc(C)c(C=O)c1F] | 320.0 (M + $NH_4^+$) |

Preparation 13 tert-Butyl 2-fluoro-4-methoxyphenoxydiphenylsilane

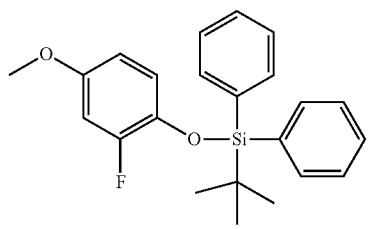 [SMILES: COc1ccc(O[Si](c2ccccc2)(c2ccccc2)C(C)(C)C)c(F)c1]

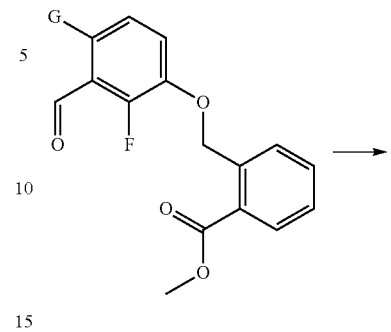

To a solution of 2-fluoro-4-methoxyphenol (25 g, 180 mmol) in DMF (350 mL 0.5 M) was added imidazole (18 g, 260 mmol) and tert-butylchlorodiphenylsilane (55 mL, 200 mmol). The reaction was stirred for 18 h at rt. The combined organic extracts were washed with water and saturated aq sodium chloride, dried over $Na_2SO_4$, filtered, and concentrated to a crude residue. The residue was purified by normal phase purification, eluting with 5:1 hexanes:ethyl acetate to give the title compound (67 g, 93% yield). $^1$H NMR (399.8 MHz, $d_6$-DMSO) δ 7.67-7.65 (m, 4H), 7.51-7.44 (m, 6H), 6.82 (dd, J=2.9, 12.7 Hz, 1H), 6.59 (t, J=9.4 Hz, 1H), 6.47 (ddd, J=9.0, 3.0, 1.4 Hz, 1H), 3.64 (s, 3H), 1.06 (s, 9H).

Scheme 5

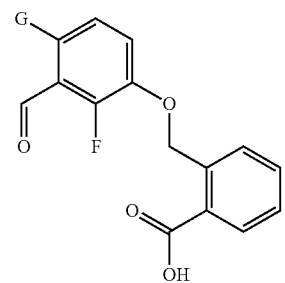

Wherein G is methyl or methoxy.

Preparation 14

2-Fluoro-3-hydroxy-6-methoxybenzaldehyde

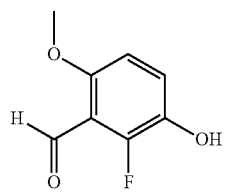

tert-Butyl 2-fluoro-4-methoxyphenoxydiphenylsilane (56 g, 150 mmol, see Preparation 13) was dissolved in 50 mL toluene and concentrated under vacuum for 18 h. The dried solid was dissolved in THF (500 mL) and cooled to −80° C. n-Butyllithium (100 mL, 170 mmol) was added rapidly to the cooled solution with a large bore cannula. After 1.5 h, DMF (25 mL, 320 mmol) was added to the solution and the ice bath was removed. After 30 min, 5N aq HCl (35 mL) was added to the reaction, then tetrabutylammonium fluoride (1M in THF, 185 mL, 185 mmol) was added. After 2.5 h, the organic layer was evaporated, acidified with 5N aq HCl, and partitioned between ethyl acetate and water (500 mL). The combined organic extracts were washed with water and saturated aq sodium chloride, dried over $MgSO_4$, filtered, and concentrated to a crude residue. The residue was purified by normal phase purification, eluting with 1:1 hexanes:ethyl acetate to give the title compound (22 g, 88% yield). MS m/z 170.8 (M+H).

Preparation 15

2-((2-Fluoro-3-formyl-4-methoxyphenoxy)methyl)benzoic Acid

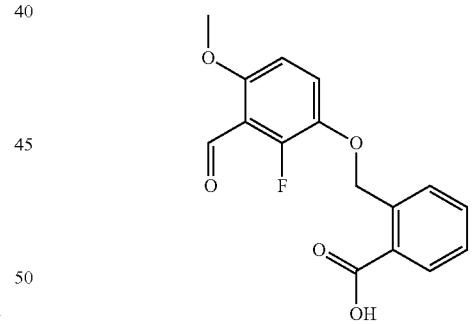

To a solution of methyl 2-((2-fluoro-3-formyl-4-methoxyphenoxy)methyl)benzoate (230 mg, 0.73 mmol) in MeOH (2 mL, 49 mmol) and THF (2 mL) was added LiOH (1.6 mL, 1.6 mmol, 1 M in water). The mixture was stirred overnight. The solvent was evaporated. The residue was diluted with water and the pH was adjusted to 6 with HCl (0.32 mL, 1.6 mmol, 5 M in water). The solid was collected by vacuum filtration and washed with water. The solid was left on the filter to dry under suction for 5 h to give the title compound (210 mg, 94% yield). MS m/z 305.0 (M+H).

The following compound was prepared in a manner essentially analogous to the procedure described in Preparation 15.

TABLE 4

| Prep. No. | Chemical Name | Structure | ES/MS (m/z) (M + H) |
|---|---|---|---|
| 16 | 2-((2-fluoro-3-formyl-4-methylphenoxy)methyl)benzoic acid | 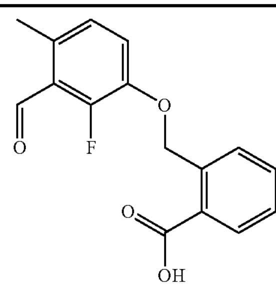 | 306.0 (M + NH₄+) |

EXAMPLE 1

4-(3-Fluoro-4-(((6aR,6bS,7S,8aS,8bS,10R,11aR,12aS,12bS)-7-hydroxy-8b-(2-hydroxyacetyl)-6a,8a-dimethyl-4-oxo-2,4,6a,6b,7,8,8a,8b,11a,12,12a,12b-dodecahydro-1H-naphtho[2',1':4,5]indeno[1,2-d][1,3]dioxol-10-yl)benzyl)benzoic Acid (Isomer 1)

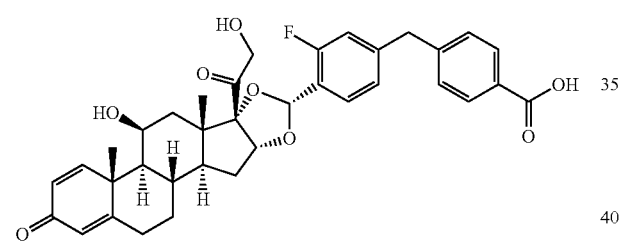

Perchloric acid (70% in water, 1.7 mL, 5 equiv.) was added to a suspension of (8S,9S,10R,11S,13S,14S,16R,17S)-11,16,17-trihydroxy-17-(2-hydroxyacetyl)-10,13-dimethyl-7,8,9,11,12,14,15,16-octahydro-6H-cyclopenta[a]phenanthren-3-one (1.5 g, 4.1 mmol, also referred to as "16alpha-hydroxyprednisolone") and 4-[(3-fluoro-4-formyl-phenyl)methyl]benzoic acid (1.00 g, 3.87 mmol, Preparation 3) in acetonitrile (20 mL) at −10° C. and was warmed to rt. After 1 h, additional acetonitrile (40 mL) and DMF (2 mL) were added to the suspension at rt. After 2 h, the reaction was quenched with saturated aqueous sodium bicarbonate and extracted with 9:1 methylene chloride:isopropanol. The organic layers were combined; dried over magnesium sulfate; filtered and concentrated under reduced pressure to give a residue. The residue was purified by reverse phase chromatography, eluting with 2:1 10 mM ammonium bicarbonate water+5% methanol:acetonitrile to give the title compound, isomer 1, peak 1 (1.48 g, 62% yield). ES/MS m/z 617.5 (M+H). ¹H NMR (400.13 MHz, d₆-DMSO) δ 7.83 (d, J=8.2 Hz, 2H), 7.50 (t, J=7.8 Hz, 1H), 7.32-7.27 (m, 3H), 7.14-7.11 (m, 2H), 6.16 (dd, J=1.8, 10.1 Hz, 1H), 5.93 (s, 1H), 5.60 (s, 1H), 4.94 (d, J=4.9 Hz, 1H), 4.89-4.72 (m, 1H), 4.48 (d, J=19.5 Hz, 1H), 4.30-4.24 (m, 1H), 4.21-4.16 (m, 1H), 4.00 (s, 2H), 2.38-2.36 (m, 1H), 2.08 (s, 3H), 1.82-1.67 (m, 5H), 1.39 (s, 3H), 1.07-0.96 (m, 2H), 0.86 (s, 3H).

EXAMPLE 2

4-(3-Fluoro-4-(((6aR,6bS,7S,8aS,8bS,10S,11aR,12aS,12bS)-7-hydroxy-8b-(2-hydroxyacetyl)-6a,8a-dimethyl-4-oxo-2,4,6a,6b,7,8,8a,8b,11a,12,12a,12b-dodecahydro-1H-naphtho[2',1':4,5]indeno[1,2-d][1,3]dioxol-10-yl)benzyl)benzoic Acid (Isomer 2)

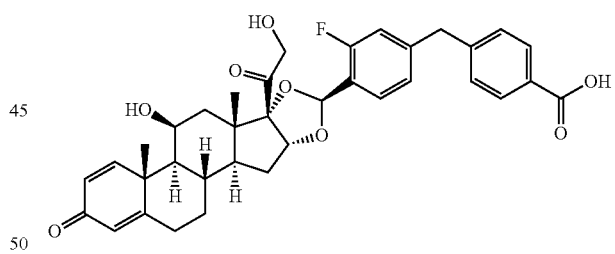

From Example 1, the residue was purified by reverse phase chromatography, eluting with 2:1 10 mM ammonium bicarbonate water+5% methanol:acetonitrile to give the title compound, isomer 2, peak 2 (122 mg, 5% yield). ES/MS m/z 617.4 (M+H). ¹H NMR (400.13 MHz, d₆-DMSO) δ 7.84 (d, J=8.2 Hz, 2H), 7.33-7.29 (m, 3H), 7.21 (t, J=7.8 Hz, 1H), 7.11-7.05 (m, 2H), 6.27 (s, 1H), 6.19-6.16 (m, 1H), 5.94 (s, 1H), 5.30 (d, J=6.4 Hz, 1H), 4.83-4.79 (m, 1H), 4.31 (s, 1H), 4.19 (d, J=19.1 Hz, 1H), 4.03-3.98 (m, 3H), 2.37-2.30 (m, 1H), 2.08-2.02 (m, 3H), 1.87-1.77 (m, 5H), 1.39 (s, 3H), 1.26-1.14 (m, 1H), 1.08-1.02 (m, 1H), 0.87 (s, 3H).

EXAMPLE 3

3-((2-Fluoro-3-((6aR,6bS,7S,8aS,8bS,10R,11aR, 12aS,12bS)-7-hydroxy-8b-(2-hydroxyacetyl)-6a, 8a-dimethyl-4-oxo-2,4,6a,6b,7,8,8a,8b,11a,12,12a, 12b-dodecahydro-1H-naphtho[2',1':4,5]indeno[1,2-d][1,3]dioxol-10-yl)-4-methylphenoxy)methyl)benzoic Acid

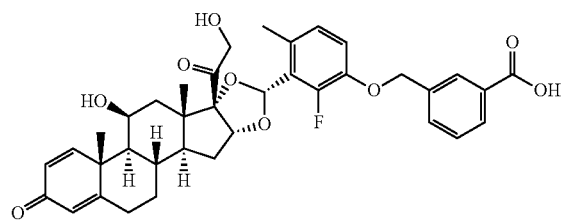

To a suspension of (8S,9S,10R,11S,13S,14S,16R,17S)-11,16,17-trihydroxy-17-(2-hydroxyacetyl)-10,13-dimethyl-7,8,9,11,12,14,15,16-octahydro-6H-cyclopenta[a]phenanthren-3-one (290 mg, 0.77 mmol, also referred to as "16alpha-hydroxyprednisolone") and tert-butyl 3-[(2-fluoro-3-formyl-4-methyl-phenoxy)methyl]benzoate (250 mg, 0.7375 mmol) in ACN (7 mL) at −10° C., was added perchloric acid (320 uL, 3.7 mmol, 70 mass % in water) dropwise. The reaction was stirred at −10° C. for 2 h. The reaction was poured into a rapidly stirring flask containing saturated aq. NaHCO₃. The mixture was stirred for 5 min and then extracted with 10% IPA/DCM (3×). The combined organic extracts were washed with brine, dried with Na₂SO₄, filtered, and concentrated to give a crude residue. The residue was purified by reverse phase chromatography, eluting with 10 mM NaHCO₃ water+5% MeOH:ACN to give a mixture of diastereomers. The mixture was subjected to chiral SFC chromatography using Chiralpak AS-H eluting with 35% EtOH (w/0.5% DMEA):65% CO₂ to give the title compound (190 mg, 40% yield). MS m/z 647.2 (M+H). ¹H NMR (399.80 MHz, d₆-DMSO): δ 7.97 (s, 1H), 7.88 (d, J=7.7 Hz, 1H), 7.58 (d, J=7.5 Hz, 1H), 7.45 (t, J=7.7 Hz, 1H), 7.32 (d, J=10.0 Hz, 1H), 7.17 (t, J=8.5 Hz, 1H), 6.92 (d, J=8.4 Hz, 1H), 6.16 (dd, J=1.8, 10.1 Hz, 1H), 5.94 (s, 1H), 5.61 (s, 1H), 5.21 (s, 2H), 4.96 (d, J=5.7 Hz, 1H), 4.81-4.81 (m, 1H), 4.47 (d, J=19.4 Hz, 1H), 4.31 (s, 1H), 4.20 (d, J=19.5 Hz, 1H), 3.47-3.41 (m, 1H), 2.30 (s, 4H), 2.18-2.14 (m, 2H), 1.86-1.75 (m, 3H), 1.64 (td, J=13.2, 5.8 Hz, 1H), 1.40 (s, 3H), 1.26-1.16 (m, 2H), 0.90-0.85 (m, 3H).

EXAMPLE 4

3-((2-Fluoro-3-((6aR,6bS,7S,8aS,8bS,10 S,11aR, 12a5,12bS)-7-hydroxy-8b-(2-hydroxyacetyl)-6a, 8a-dimethyl-4-oxo-2,4,6a,6b,7,8,8a, 8b,11a,12,12a, 12b-dodecahydro-1H-naphtho[2',1':4,5]indeno[1,2-d][1,3]dioxol-10-yl)-4-methylphenoxy)methyl)benzoic Acid

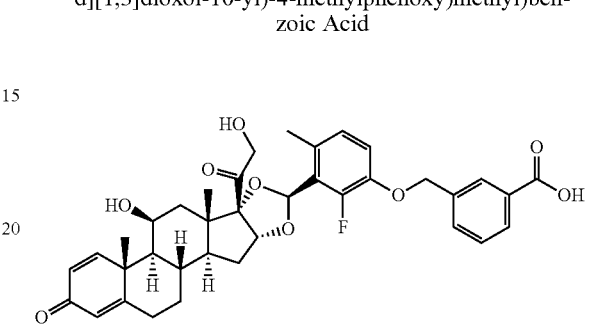

Chiral SFC purification described in Example 3 gave the title compound as the second diastereomer (61 mg, 13% yield). MS m/z 647.3 (M+H). ¹H NMR (399.80 MHz, DMSO): δ 7.97 (s, 1H), 7.87 (d, J=7.7 Hz, 1H), 7.59 (d, J=7.7 Hz, 1H), 7.47 (t, J=7.7 Hz, 1H), 7.34-7.32 (m, 1H), 7.17-7.13 (m, 1H), 6.90 (d, J=8.4 Hz, 1H), 6.34 (s, 1H), 6.18 (dd, J=1.9, 10.0 Hz, 1H), 5.95 (s, 1H), 5.31 (d, J=6.7 Hz, 1H), 5.22-5.15 (m, 2H), 4.78 (d, J=2.6 Hz, 1H), 4.32 (d, J=18.9 Hz, 2H), 4.02 (d, J=19.0 Hz, 1H), 3.17 (s, 1H), 2.40-2.39 (m, 2H), 2.22 (s, 3H), 2.11-2.08 (m, 2H), 1.91-1.86 (m, 2H), 1.40 (s, 3H), 1.31-1.19 (m, 3H), 0.88 (s, 3H).

The following compounds listed in Table 5 were prepared in a manner essentially analogous to the method described in Examples 3 and 4 utilizing the corresponding aldehyde starting material as indicated in the table. Purification of final products was performed essentially by the following methods:

A. C18 column using eluent 10 mM NH₄HCO₃ in water+5% MeOH:ACN

B. C18 column using eluent 0.1% FA in water:ACN

C. Chiral SFC using Chiralcel OJ-H eluting with MeOH+0.5% DMEA:CO₂

TABLE 5

| Ex. No. | Structure | ES/MS (m/z) (M + H) | Purification method and aldehyde starting material |
|---|---|---|---|
| 5 | 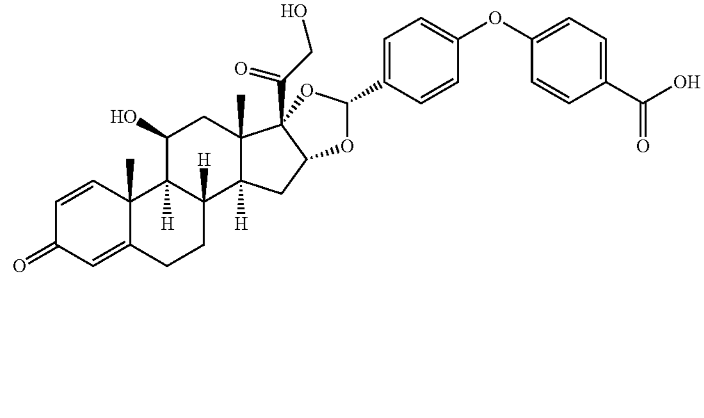 | 601.4 | A Prep. 4 |

TABLE 5-continued
| Ex. No. | Structure | ES/MS (m/z) (M + H) | Purification method and aldehyde starting material |
|---|---|---|---|
| 6 | 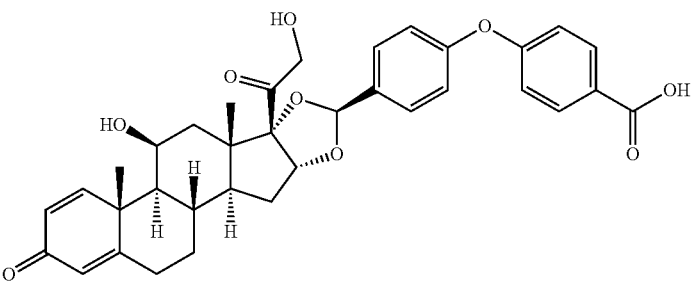 | 601.4 | A Prep. 4 |
| 7 | 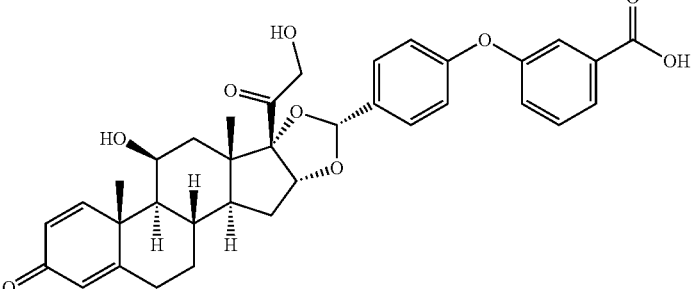 | 601.4 | A Prep. 5 |
| 8 | 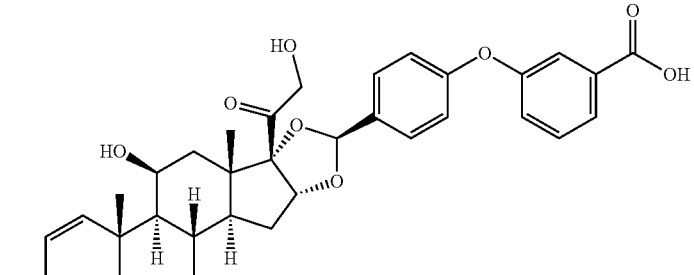 | 601.4 | A Prep. 5 |
| 9 | 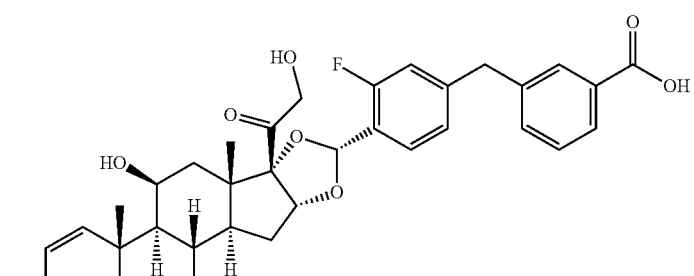 | 617.2 | B Prep. 2 |

TABLE 5-continued

| Ex. No. | Structure | ES/MS (m/z) (M + H) | Purification method and aldehyde starting material |
|---|---|---|---|
| 10 | 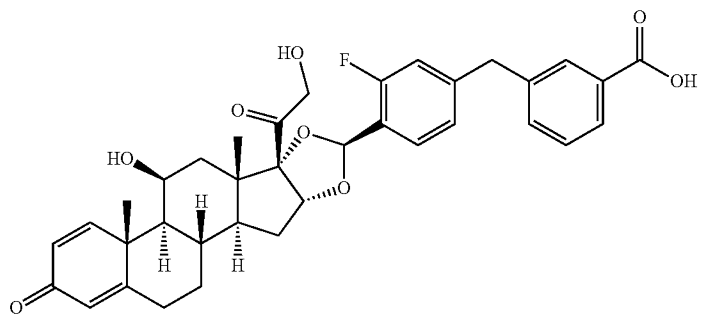 | 617.3 | B Prep. 2 |
| 11 | 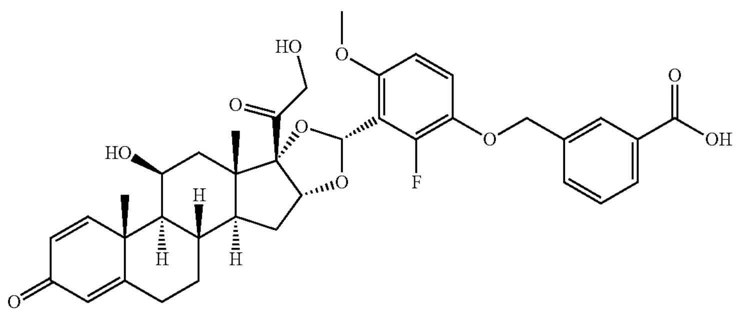 | 663.4 | A, C Prep. 10 |
| 12 | 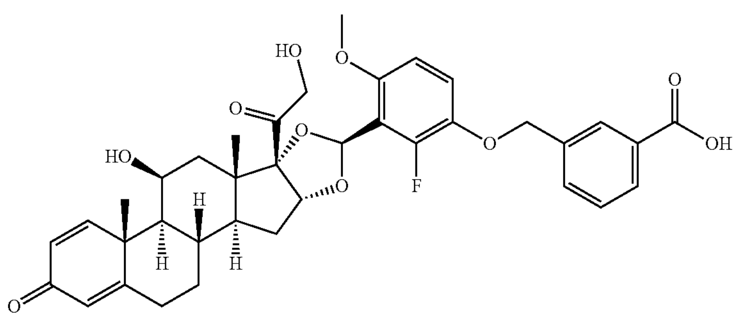 | 663.4 | A, C Prep. 10 |
| 13 | 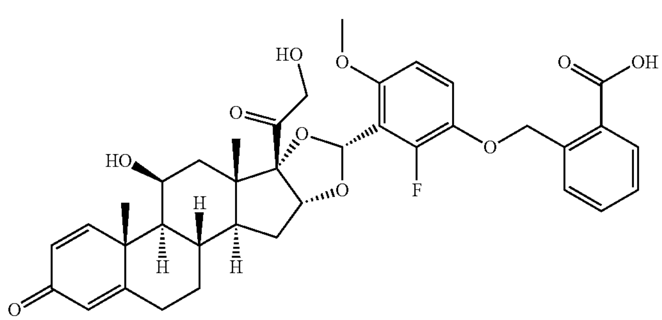 | 663.4 | B Prep. 11 |

TABLE 5-continued

| Ex. No. | Structure | ES/MS (m/z) (M + H) | Purification method and aldehyde starting material |
|---|---|---|---|
| 14 | 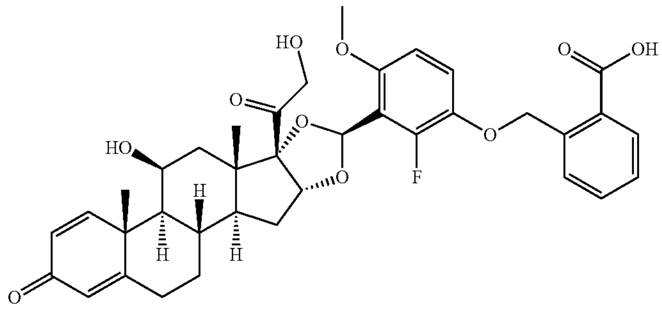 | 663.4 | B Prep. 11 |
| 15 | 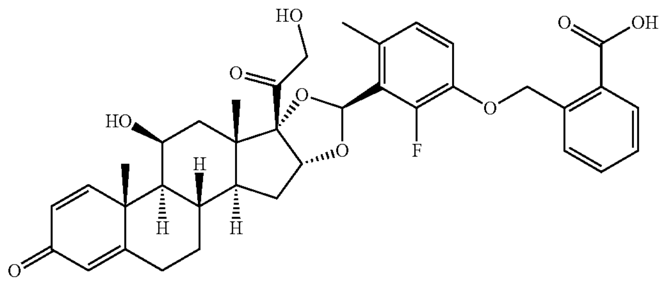 | 647.4 | B Prep. 16 |

Structural Assignment by NMR

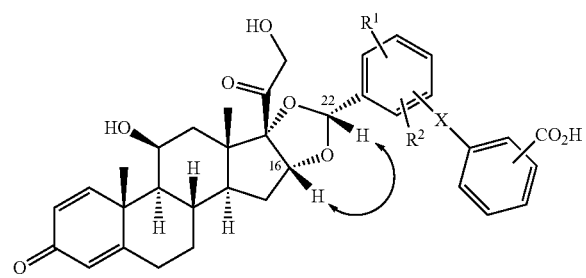

Two dimensional through-space ROE NMR analysis of acetal isomers consistently gave a cross peak for H22 (acetal) and H16 in the R configuration. Alternatively, H22 in the S configuration consistently gave about 1 ppm larger shift. All other compounds were assigned essentially by the same method.

hGR CoActivator Recruitment Assay

The activity of glucocorticoid compounds was measured using the LanthaScreen TR-Fret GR Coactivator Assay from Life Technologies (A15899). The compounds were acoustically transferred to an assay plate in a 3-fold 10-point serial dilution with a top concentration of 200 nM. Ten microliters of a 2× solution of GR-LBD was added to the compound plate and incubated for 10 min. Then ten microliters of a 2× solution of Fluoresein-SRC1-4 and Tb labelled anti-GST antibody was added to the plate. The plate was incubated in the dark for two hours and then read on an Envision plate reader, with excitation at 340 nm and emission at 520 nm (Fluorescein) and 490 nm (Terbium). The emission ratio of 520/490 was analyzed in Genedata. To obtain percent activity, the data was compared to a negative control of DMSO and positive control of 404 dexamethasone.

Following the procedure as essentially described above, the compound of Example 1 provided a relative $IC_{50}$ of 2.14 nM, the compound of Example 2 provided a relative $IC_{50}$ of 4.50 nM, and the compounds of Examples 3-9, 11, 12, 14, and 15 each provided a relative $IC_{50}$ of less than 200 nM. Examples 10 and 13 each provided a relative $IC_{50}$ greater than 200 nM.

What is claimed is:
1. A compound of the formula:

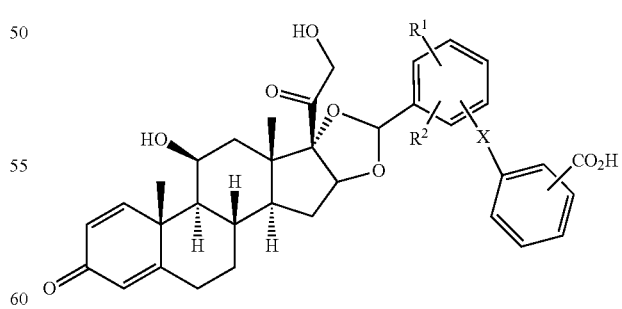

wherein $R^1$ is H, halogen, C1-C3 alkyl, or C1-C3 alkoxy;
$R^2$ is H or halogen; and
X is O, $OCH_2$, or $CH_2$,
or a pharmaceutically acceptable salt thereof.

2. The compound according to claim 1 wherein $R^1$ is F, or a pharmaceutically acceptable salt thereof.

3. The compound according to claim 1 wherein $R^1$ is $CH_3$, or a pharmaceutically acceptable salt thereof.

4. The compound according to claim 1 wherein $R^1$ is $OCH_3$, or a pharmaceutically acceptable salt thereof.

5. The compound according to claim 1 wherein $R^1$ is H, or a pharmaceutically acceptable salt thereof.

6. The compound according to claim 1 wherein $R^2$ is H, or a pharmaceutically acceptable salt thereof.

7. The compound according to claim 1 wherein $R^2$ is F, or a pharmaceutically acceptable salt thereof.

8. The compound according to claim 1 wherein X is $CH_2$, or a pharmaceutically acceptable salt thereof.

9. The compound according to claim 1 wherein X is O, or a pharmaceutically acceptable salt thereof.

10. The compound according to claim 1 wherein X is $OCH_2$, or a pharmaceutically acceptable salt thereof.

11. The compound according to claim 1 wherein the compound is of the formula:

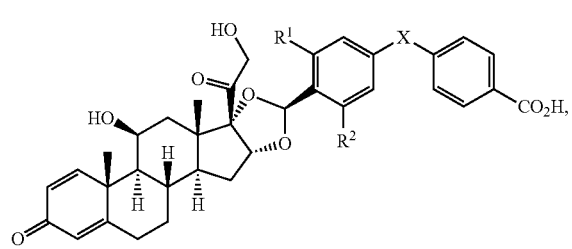

or a pharmaceutically acceptable salt thereof.

12. The compound according to claim 1 wherein the compound is of the formula:

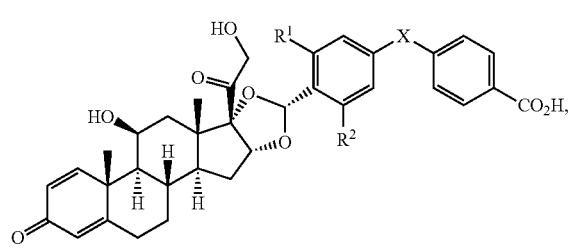

or a pharmaceutically acceptable salt thereof.

13. The compound according to claim 1 wherein the compound is:

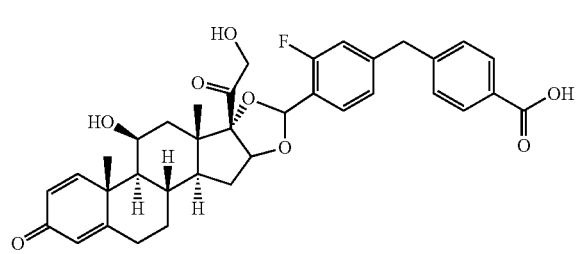

or a pharmaceutically acceptable salt thereof.

14. The compound according to claim 1, wherein the compound is:

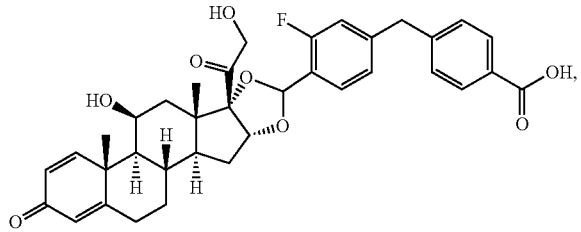

or a pharmaceutically acceptable salt thereof.

15. The compound according to claim 1, wherein the compound is:

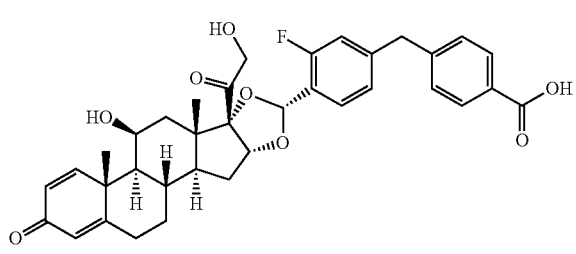

or a pharmaceutically acceptable salt thereof.

16. The compound according to claim 15 which is:

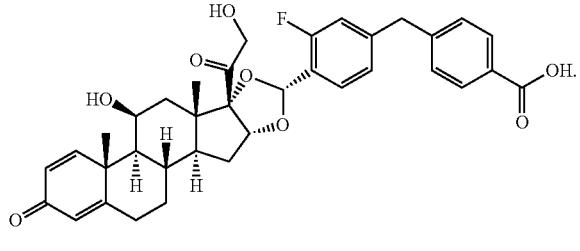

17. The compound according to claim 1 wherein the compound is:

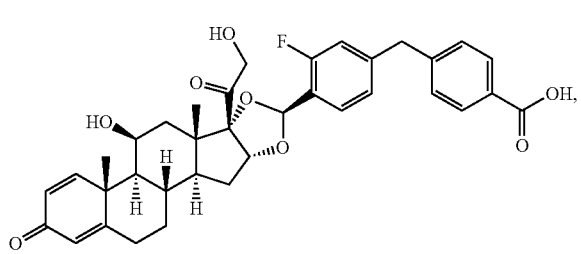

or a pharmaceutically acceptable salt thereof.

18. The compound according to claim 17 which is:
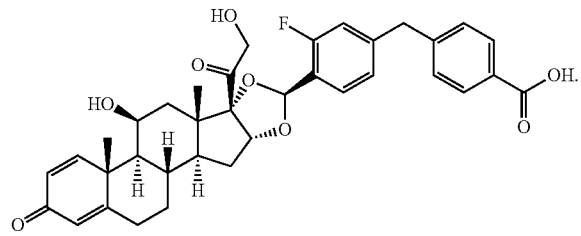
19. The compound of claim 1 selected from the group consisting of:
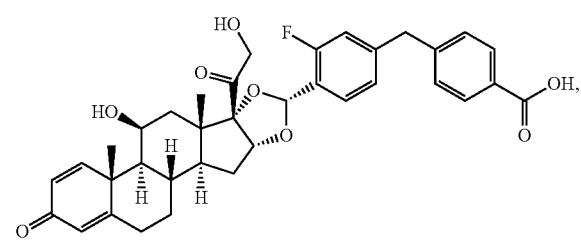
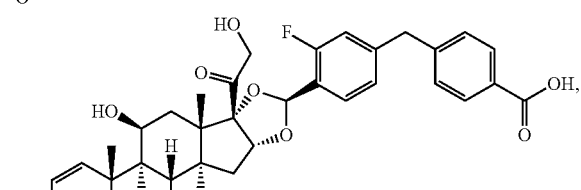
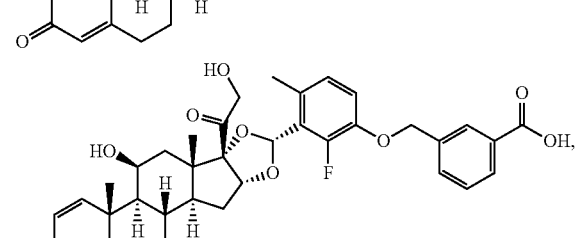
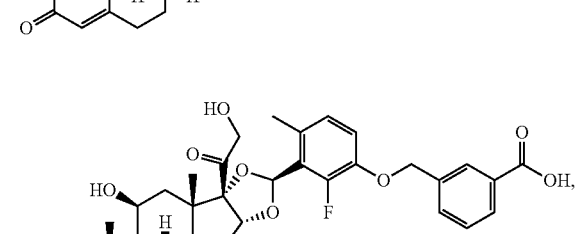
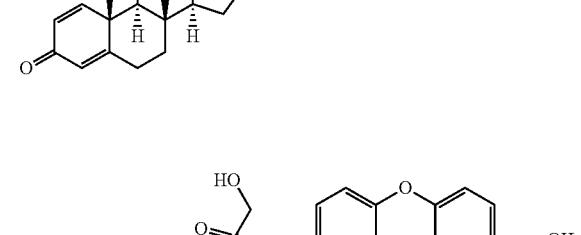
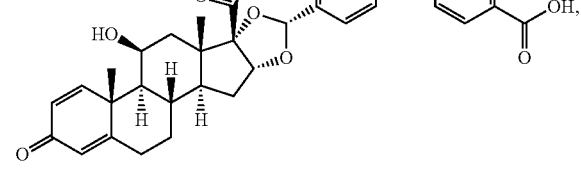
-continued
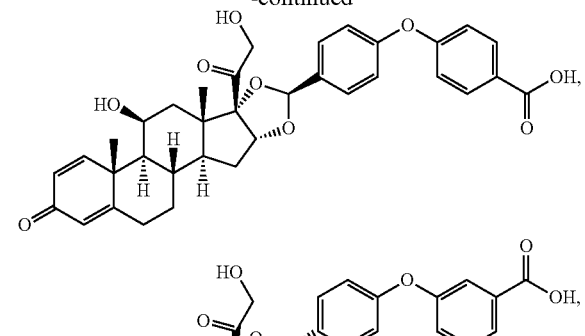

-continued

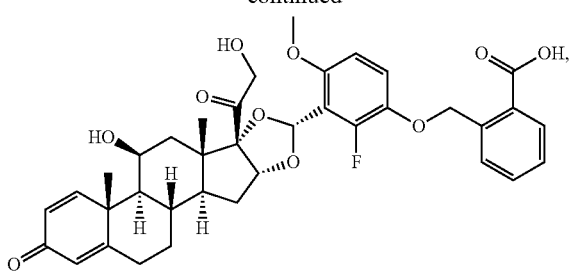

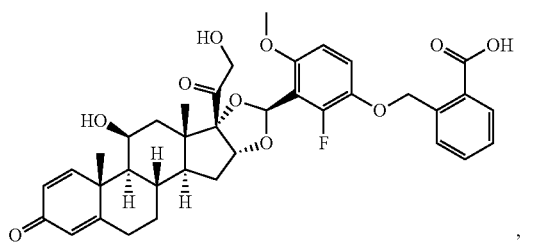
, and

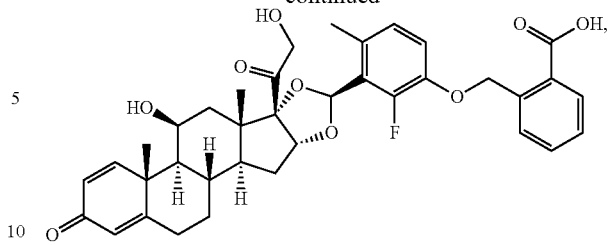

and the pharmaceutically acceptable salts thereof.

20. A method of treating atopic dermatitis in a patient, comprising administering to a patient in need of such treatment an effective amount of a compound according to claim 1, or a pharmaceutically acceptable salt thereof.

21. A method of treating rheumatoid arthritis in a patient, comprising administering to a patient in need of such treatment an effective amount of a compound according to claim 1, or a pharmaceutically acceptable salt thereof.

22. A method of treating lupus nephritis in a patient, comprising administering to a patient in need of such treatment an effective amount of a compound according to claim 1, or a pharmaceutically acceptable salt thereof.

23. A pharmaceutical composition, comprising a compound or a pharmaceutically acceptable salt thereof, according to claim 1 with one or more pharmaceutically acceptable carriers, diluents, or excipients.

24. A process for preparing a pharmaceutical composition, comprising admixing a compound or a pharmaceutically acceptable salt thereof according to claim 1 with one or more pharmaceutically acceptable carriers, diluents, or excipients.

* * * * *

UNITED STATES PATENT AND TRADEMARK OFFICE
CERTIFICATE OF CORRECTION

PATENT NO. : 11,618,767 B2  
APPLICATION NO. : 17/700824  
DATED : April 4, 2023  
INVENTOR(S) : Ryan Edward Stites and Jacqueline Mary Wurst Page 1 of 2

It is certified that error appears in the above-identified patent and that said Letters Patent is hereby corrected as shown below:

In the Claims

In Column 32, Lines 30-39, in Claim 19, delete:

"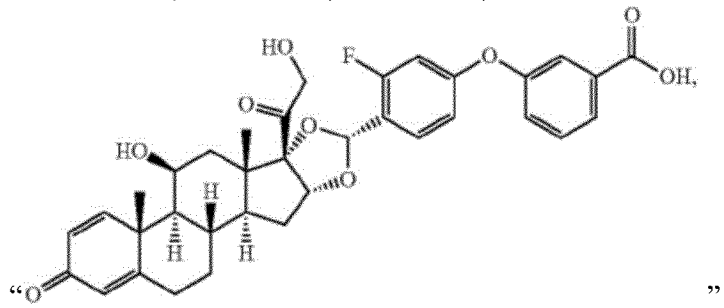"

And insert:

--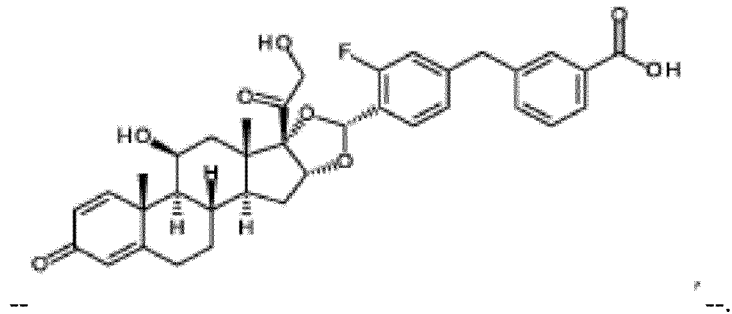--.

Signed and Sealed this  
First Day of August, 2023

Katherine Kelly Vidal  
*Director of the United States Patent and Trademark Office*

CERTIFICATE OF CORRECTION (continued)

In Column 32, Lines 40-49, in Claim 19, delete:

"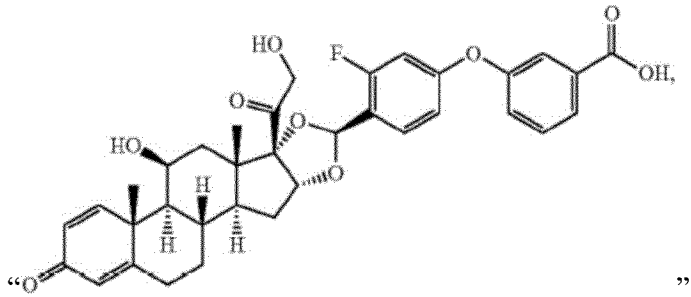"

And insert:

--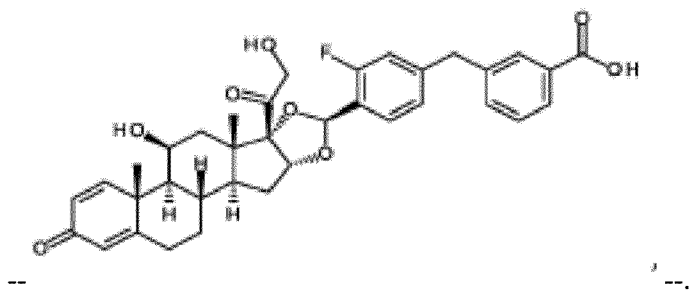--.